(12) United States Patent
Skog et al.

(10) Patent No.: US 6,290,687 B1
(45) Date of Patent: Sep. 18, 2001

(54) FASTENER MEANS FOR JOINING TOGETHER OPPOSING FRONT AND REAR SIDE-PARTS OF AN ABSORBENT ARTICLE

(75) Inventors: Terje Skog, Nykirke (NO); Anna Karin Jönbrink, Lerum (SE)

(73) Assignee: SCA Hygiene Products AB, Goteburg (SE)

( * ) Notice: Subject to any disclaimer, the term of this patent is extended or adjusted under 35 U.S.C. 154(b) by 0 days.

(21) Appl. No.: 09/333,979

(22) Filed: Jun. 16, 1999

Related U.S. Application Data

(62) Division of application No. 08/973,973, filed on Mar. 26, 1998, now Pat. No. 6,123,695.

(51) Int. Cl.$^7$ ....................................................... A61F 13/15
(52) U.S. Cl. ........................... 604/391; 604/386; 604/390; 604/385.01; 24/614; 24/618
(58) Field of Search ............................... 24/442, 443, 450, 24/174, 629, 615, 614, 618; 604/386, 385.1, 391

(56) References Cited

U.S. PATENT DOCUMENTS

| | | |
|---|---|---|
| 2,837,096 | 6/1958 | Leveillee . |
| 4,408,375 | 10/1983 | Skobel . |
| 4,688,337 * | 8/1987 | Dillner et al. .......................... 24/616 |
| 4,701,170 | 10/1987 | Wilson et al. . |
| 4,801,298 | 1/1989 | Sorenson et al. . |
| 5,170,539 * | 12/1992 | Lundstedt et al. ...................... 24/196 |

FOREIGN PATENT DOCUMENTS

| | | |
|---|---|---|
| 2 322 492 | 11/1974 | (DE) . |
| 0 095 656 | 12/1983 | (EP) . |
| 507024 | 9/1938 | (GB) . |
| 1083211 | 9/1967 | (GB) . |
| 1 428 572 | 3/1976 | (GB) . |
| 1428572 | 3/1976 | (GB) . |
| 2 176 832 | 1/1987 | (GB) . |
| 2 262 962 | 7/1993 | (GB) . |

* cited by examiner

*Primary Examiner*—Aaron J. Lewis
*Assistant Examiner*—Michele Kidwell
(74) *Attorney, Agent, or Firm*—Burns, Doane, Swecker & Mathis, L.L.P.

(57) ABSTRACT

A fastener joins together opposing front and rear side-parts and respectively of an absorbent article in the form of a diaper or the like, so as to form an encircling waistband. The article includes a central part having an absorbent body, and front and rear pliable side-parts which extend from respective sides of the central diaper part. The fastener includes two mutually coacting first and second fastener elements of which the first element is attached to a front side-part and the second element is attached to the rear side-part on the same side of the central part as its associated first element. The first fastener element or the second fastener element includes a fastening portion which projects out from the perimeter of the waistband and which can be inserted into an insertion opening in the associated second or first fastener element. One of the first or the second fastener elements includes at least one locking member which extends generally perpendicular to the insertion direction of the fastener portion and coacts with a locking aperture in the second fastener element when the fastener portion is inserted.

8 Claims, 2 Drawing Sheets

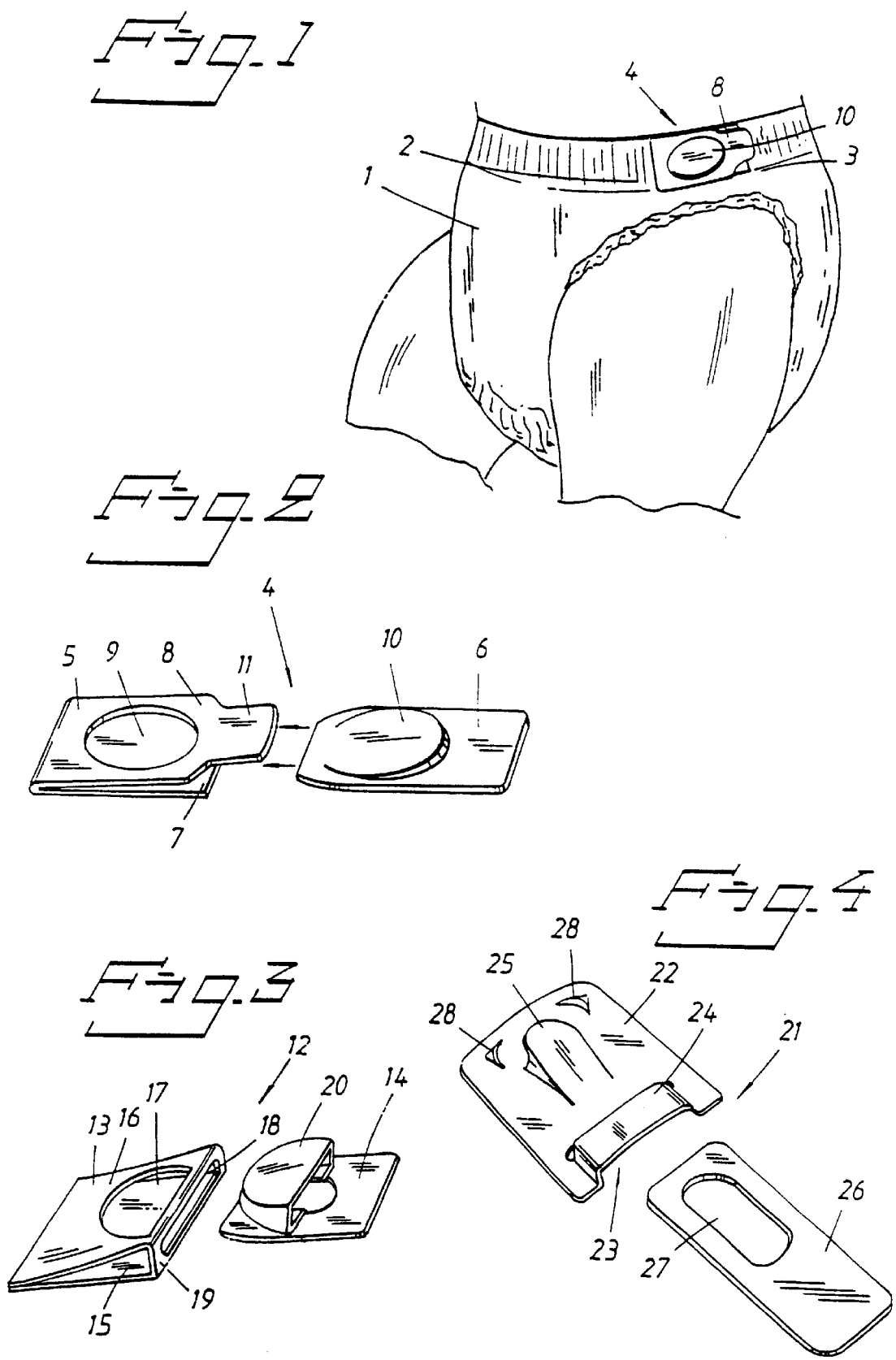

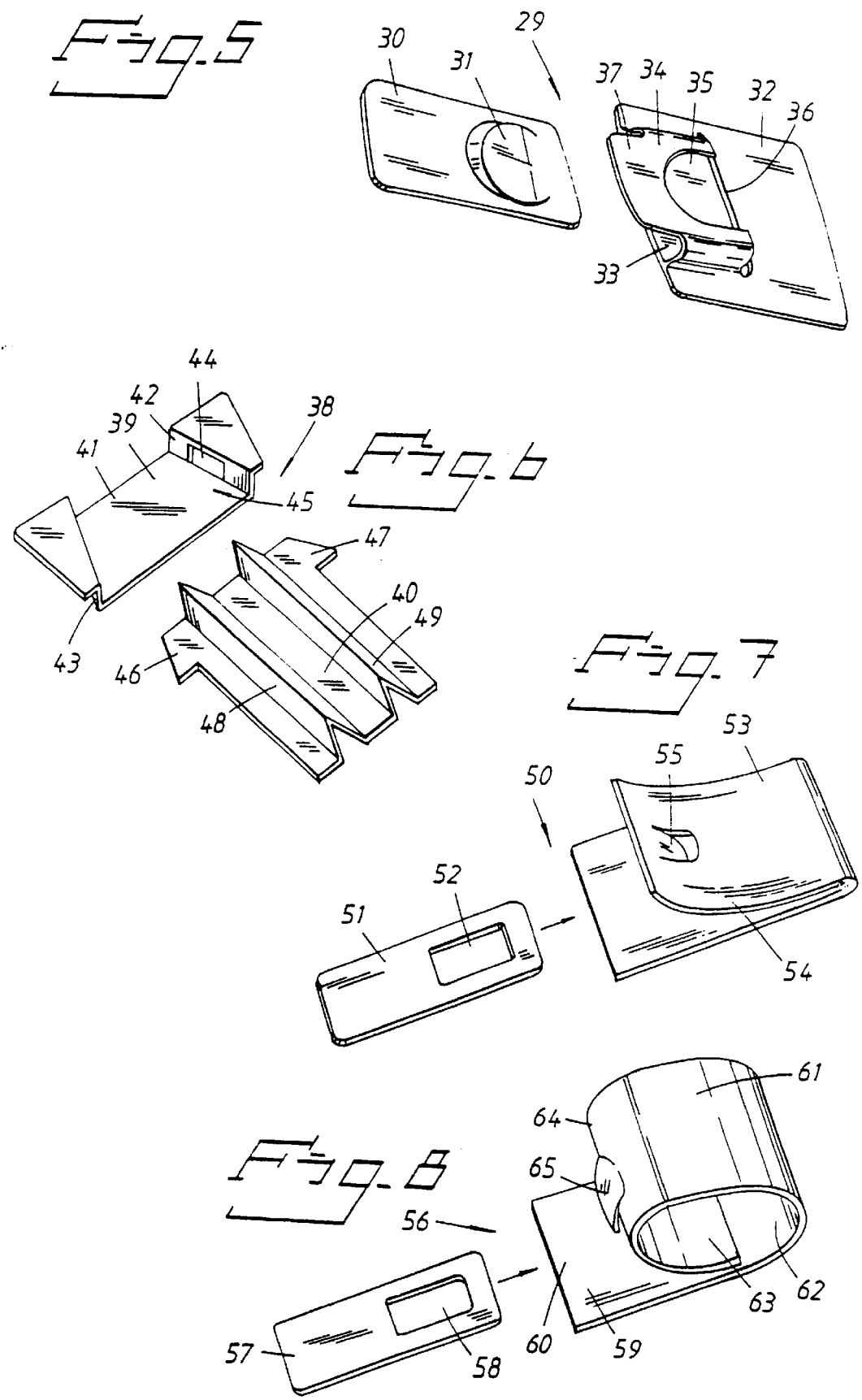

FASTENER MEANS FOR JOINING TOGETHER OPPOSING FRONT AND REAR SIDE-PARTS OF AN ABSORBENT ARTICLE

This application is a divisional of application Ser. No. 08/973,973, filed Mar. 26, 1998 now U.S. Pat. No. 6,123, 695.

The present invention relates to fastener means for fastening together opposing front and rear side-parts of an absorbent article, such as a diaper or like article, so as to form an encircling waistband, said article comprising a central part which includes an absorbent body, and front and rear flexible side-parts which extend from both sides of the central part, wherein the fastener means comprise two mutually coacting first and second parts of which the first part is attached to a front side-part and the second fastener element is attached to the rear side-part of the article, on the same side of the central part as the associated first fastener element.

The side-parts of diapers are normally fastened together with the aid of fastener tabs which are firmly anchored to one side-part of the diaper and which when donning the diaper are fastened to the other side-part of the diaper with the aid of a releasable and refastenable type of adhesive. The side-part onto which the fastener tab is fastened when putting on the diaper may be reinforced in different ways, to enable the fastener means to be released and refastened repeatedly without damaging the diaper casing sheet. One problem with the use of adhesive tape is that contaminants, such as baby talcum, are liable to stick to the adhesive and therewith impair its adhesiveness. Furthermore, many users lack a clear indication as to where the fastener tabs shall be fastened in order to obtain a suitable tight fit around the waist of the wearer. There is therefore a need for mechanical fasteners for fastening the side-parts of diapers together. One such mechanical fastener means is known from U.S. Pat. No. 4,701,170, which describes a diaper whose side-parts are fastened together with the aid of mutually coacting resilient hock devices.

The object of the present invention is to provide mechanical fastener means which will satisfy the aforesaid need and which can be easily opened and closed.

In accordance with the invention, this object is achieved with fastener means of the kind defined in the introduction which are characterized in that the first or the second part of the fastener means includes a fastener portion which projects out in the circumferential direction of the waist-band and which can be inserted into an opening in its associated second or first fastener element, and in that one of the first and the second fastener elements includes at least one locking member which extends in a direction generally perpendicular to the direction in which the fastener portion is inserted and coacts with a locking aperture in the second fastener element in the inserted position of the fastener portion. A mechanical fastener of this kind can be released and fastened very easily.

In the case of one preferred embodiment of the invention, the locking member and the locking aperture coacting therewith are configured so that the first and the second fastener elements can only be fastened, or locked, together in one single relative position. The locking member projects out at right angles to the plane of the waistband and the insertion aperture is defined by the space between two mutually divergent walls on that part of the fastener means which includes the locking aperture. The locking member is comprised of a raised portion which projects out from a flat undersurface and which has on its outermost part a bead which extends at least around the rear edge of the raised portion as seen in the insertion direction.

In the case of one variant, the locking member projects out at right angles to the insertion direction and in the plane of the waistband or waist opening.

The invention will now be described in more detail with reference to the accompanying drawings, in which FIG. 1 is a perspective view of a donned diaper provided with a first embodiment of inventive fastener means;

FIG. 2 is a perspective view of the fastener means on the diaper shown in FIG. 1, and shows the fastener means in a separated state; and FIGS. 3–8 illustrate further embodiments of inventive fastener means in views similar to the view shown in FIG. 2.

FIG. 1 illustrates a donned diaper 1, where the diaper has been brought to a pants-like form by closing the front and the rear side-parts 2, 3 of the diaper together with the aid of inventive fastener means 4. FIG. 1 shows only the fastener means attached to the left side of the diaper. The diaper 1 is of typical construction and includes an inner, liquid-permeable casing sheet, an outer liquid-impermeable backing sheet and an absorbent body enclosed between said sheets. The diaper has conventionally a central part and front and rear side-parts which project out from both sides of the central part. The present invention can be understood without describing the construction of the diaper 1 in depth and the diaper will not therefore be described in detail in this document.

FIG. 2 illustrates the left-hand fastener means 4 shown in FIG. 1 in larger scale and in a separated or released state. The fastener means 4 comprises a first fastener element 5 which is attached to the front side-part 2 of the diaper, and a second fastener element 6 which is attached to the rear side-part 3 of said diaper. The first fastener element 5 includes an inner wall 7 and an outer wall 8 wherein the walls diverge relative to one another from the one end of the first fastener element, such that said walls will be mutually spaced at the other end of said part. The upper wall has a through-penetrating aperture 9. The second fastener element 6 is comprised of a generally rectangular plate having a raised portion 10 which extends essentially from one end of the plate, the plate insertion end, slightly in towards the other end of the plate, the fastening end. The thickness of the raised portion 10 increases in a direction towards the fastening end and the thickness at its highest part is greater than the greatest distance between the walls 7, 8 of the first fastener element 5 within the region of the aperture 9. The raised portion 10 has a shape which is complementary to the shape of the aperture 9, at least within the region of the highest edge of said aperture. The fastener elements 5, 6 are preferably made from an elastic or resilient material, for instance a thermoplastic material. In this latter case, the fastener elements may be vacuum-formed, which is particularly preferred. As the front end of the illustrated fastener element 6 is inserted between the walls of the fastener element 5 in the insertion direction arrowed in FIG. 2, the wall 8 will be flexed outwardly to enable the raised portion 10 to pass. When the rear edge of the raised portion 10, as seen in the insertion direction, has passed the rear edge of the aperture 9, as seen in the insertion direction, the resiliency of the wall 8 will cause the wall to spring back to its earlier position, wherewith part of the raised portion 10 will project out through the aperture 9 and beyond the wall 8, so as to lock the fastener elements 5 and 6 together.

According to one variant, the raised portion 10 is provided with a bead or the like at least around the highest part of its upper edge, to eliminate the risk of the mechanical connection between the fastener elements 5 and 6 being released unintentionally. Because the tensioning force acting on the side-parts of the diaper strives to separate the side-parts, the highest part of the edge of the aperture 9 will press against the highest part of the raised portion 10 beneath the bead when the diaper is worn.

The mechanical connection between the fastener elements 5 and 6 can be released simply by lifting the outer wall 8 so as to move the aperture 9 out of engagement with the raised portion 10. To this end, the upper wall 8 is preferably terminated with a grip tab 11. After having released the raised portion 10 from the aperture 9 in the upper wall, the diaper side-parts will be mutually separated by the tension force acting therein, and the fastener element 6 will be moved relative to the fastener element 5 in a direction opposite to the insertion direction. The diaper will preferably be provided with waist elastic, to increase the tensioning or tightening force around the waist opening. Instead of lifting the outer wall 8, the raised portion 10 may be brought out of engagement with the aperture 9 by pressing the raised portion 10 down towards the bottom wall 7. The raised portion 10 may be made thin, in order to facilitate its depression towards the bottom wall. The fastener means provided on the right side of the diaper shown in FIG. 1 is identical to the described fastener means 4. Naturally, the fastener element 6 may be attached to the front side-part of the diaper instead of. to its rear side-part as in the illustrated case, and the fastener element 5 may be attached to the rear side-part of said diaper instead of to its front side-part.

FIG. 3 illustrates a second embodiment of an inventive fastener means, generally referenced 12. Similar to the fastener means 4, the fastener means 12 includes two fastener elements 13, 14, of which one is attached to the front side-part of a diaper and the other is attached to the rear side-part thereof. The fastener element 13 is comprised of a rectangular piece of material which has been folded in a manner to obtain a triangular cross-sectional shape. The free ends of the bottom wall 15 and the top wall 16 of the folded piece of material are attached to one another in some suitable way. The top wall 16 includes a generally semicircular aperture 17 and an insertion opening 18 has been provided in the wall 19 at that end of the folded piece which is distal to the free ends of the walls 15, 16. The fastener element 14 is comprised of a plate that includes a raised portion 20 having a shape which is complementary to the aperture 17, as seen from above in FIG. 3. The raised portion 20 is hollow and has a pistol-holster configuration and can therefore be easily pressed together.

The fastener elements 13, 14 are secured to one another, by inserting the front end of the fastener element 14 in FIG. 3 into the insertion opening 18. When the rear end of the compressed raised portion 20 has just passed the rear edge of the aperture 17, the resiliency of the walls of the raised portion 20 will lift an upper part of said raised portion above the plane of the aperture 17 and therewith lock the fastener elements 13, 14 together. The mechanical connection between the fastener elements 13, 14 is released by simply pressing down the raised portion 20, wherewith the fastener elements 13, 14 will be mutually separated by the tensioning force acting thereon. It is preferred that the upper edge of the insertion opening 18 is flush with the inner surface of the upper wall 16, so as to facilitate release of the fastener means.

FIG. 4 illustrates a third embodiment of an inventive fastener means, generally referenced 21. The principle difference between the earlier described embodiments and the FIG. 4 embodiment is that the raised portion and the insert opening are placed on the same part of the fastener means instead of on separate fastener elements as in the case of the two previously described embodiments. Thus, the fastener means 21 includes a generally rectangular first fastener element 22 which has an insertion opening 23 formed by an upwardly projecting stirrup-shaped part 24, and a raised portion 25. The second fastener element 26 has the form of a tongue provided with an aperture 27. The raised portion 25 will preferably include a bead which extends along the upper part of its front end as seen in FIG. 4 to prevent the tongue being moved unintentionally at right angles to the plane of the first fastener element 22 in the fastened state of the fastener means 21. The fastener element 22 may optionally be provided with stop means in the form of projections 28, against which the front side-edge parts of the tongue will abut when the fastener means is fastened. Alternatively, instead of stop means, the fastener element 22 may be provided with slots or outwardly projecting tab-like parts for receiving the front side-edge parts of the tongue and therewith prevent movement of the front edge of said tongue in the insertion direction when the fastener means is fastened.

FIG. 5 illustrates a fourth embodiment of an inventive fastener means, generally referenced 29. The fastener means 29 is comprised of a generally rectangular first fastener element 30 which includes a raised portion 31, which may advantageously have a bead (not shown in the Figure), at least along the upper, left-hand edge thereof as seen in the Figure, and a generally rectangular and flat second fastener element 32. The second fastener element 32 includes an insertion opening 33 which is delimited by a stirrup-like part 34 which projects upwards in the Figure. The upper wall of the stirrup-like part includes an aperture 35 whose shape is complementary to a front part of the raised portion 31. The element 32 also includes stop means 36 in the form of an upstanding edge or the like, which coacts with the front end of the first element 30, as seen in the Figure, to prevent said element moving forwards in relation to the stirrup-like part 34 when the fastener means 29 is fastened, such as to bring the rear edge of the raised portion 31 out of engagement with the aperture 35. The stirrup-like part 34 is also advantageously provided with a grip tab 37 for facilitating the unlocking or release of a fastened or locked fastener means 29.

FIG. 6 illustrates a fifth embodiment of an inventive fastener means, generally referenced 38. The fastener means is comprised of a first fastener element 39 and a second fastener element 40. The first fastener element 39 includes a bottom plate 41 which has the shape of an isosceles parallel-trapezium, or parallel-trapezoid, and has two walls 42, 43 upstanding from the non-parallel edges of the plate. Each of the walls 42, 43 has provided therein a locking aperture 44, of which only one can be seen in the Figure, said apertures being opposite one another. The fastener element 39 also includes an insertion opening 45 which is delimited by the bottom plate and the two upstanding walls. When seen from above, the fastener element 40 has the shape of an arrow with a truncated point, this pointed part forming two outwardly projecting locking hooks 46, 47. Two upstanding folds 48, 49 extend in the longitudinal direction of the fastener element 40, along the full length of the arrowed part. The side edges of the locking hooks are inclined in the longitudinal direction at the same angles as the angles at which the equal sides of the parallel-trapezium are inclined to a line that extends at right angles to the parallel sides of said trapezium. When inserting the fastener element 40 through the insert opening 45, the side edges of the locking hooks will run against the walls 42, 43 while compressing the walls of the folds 48, 49 until the locking hooks snap into the locking apertures 44 in the side walls of the part 39, wherewith the fold walls separate from one another by virtue of their resiliency. The mutually fastened elements 39, 40 can be easily separated from one another, by simply pressing together the folds 48, 49.

In the case of one variant, each wall 42, 43 of the FIG. 6 embodiment may include two or more pairs of mutually opposing apertures so as to enable the fastener elements 39, 40 to be locked together in selected separate positions in the insertion direction. In this regard, the fastener element 40 may be provided with broader folds or with a larger number of folds, so as to achieve an effective degree of compression of the fastener element 40.

The fastener means 38 may also be manufactured from a thermoplastic material, such as a thermosetting resin, board or some other foldable material.

FIG. 7 illustrates a sixth embodiment of an inventive fastener means, generally referenced 50. The fastener means includes a tongue-like first fastener element 51 provided with an aperture 52, and a second fastener element 53. The fastener element 53 is comprised of a folded strip. The free end of the upper wall 54 is curved and includes a downwardly protruding locking tab 55 which coacts with the aperture 52 in the first fastener element 51 when fastening or closing the fastener means 50. The fastener means 50 is opened conveniently, by lifting the upper wall 54 until the locking tab 55 leaves the aperture 52.

FIG. 8 illustrates a seventh embodiment of an inventive fastener means, generally referenced 56. The fastener means includes a tongue-like first element 57 provided with an aperture 58, and a second element 59. The fastener element 59 is comprised of a strip of material and includes a bottom wall 60, a top wall 61, an arcuate part 62 which mutually connects the top and the bottom walls, and an end part 63 which connects with the top wall 61 through an arcuate part 64, and terminates with a part that extends between the top and the bottom walls. The arcuate part includes a locking tab 65 which projects down essentially at right angles to the tongue 57 insertion direction. The fastener means 56 is fastened in the same way as the fastener means 50 of the FIG. 7 embodiment, and is released by lifting the top wall 61.

The fastener means 50 and 56 illustrated respectively in FIGS. 7 and 8 can be produced very readily from strip material, since the process of manufacture solely involves punching and folding operations. For instance, the locking tabs 55 and 65 are first punched from the fastener elements 53 and 59 and when subsequently folding the curved portions of these fastener elements, the locking tabs will automatically take the positions shown in the Figures.

All of the aforedescribed fastener means are fastened, locked, by inserting a part of one fastener element into an opening in the other fastener element, wherewith a locking member automatically snaps into a locking aperture. It is therefore extremely easy to fasten a fastener means that has been constructed in accordance with the invention. Furthermore, all of the fastener means described can be released by moving the locking member out of engagement with its locking aperture with a simple movement of the hand, wherein the tension force in the diaper to which the fastener means is attached will cause the two fastener elements to separate from one another. An inventive fastener means can thus be opened very easily.

All of the illustrated and described fastener means may be produced from sheet material, suitably by vacuum-forming, which is favourable from a cost aspect. Naturally, other methods of manufacture are conceivable, such as moulding or injection-moulding processes, although when practicing these alternative methods the fastener means cannot be made as thin as when vacuum-forming sheet material. It is also possible to use other materials than plastic materials, provided that such materials are sufficiently flexible or pliable to conform to the body contours of the wearer of the diaper, and providing that the raised portion and/or the fastener element that contains the locking aperture will have resilient properties.

It will be understood that the illustrated and described exemplifying embodiments can be modified within the scope of the invention, particularly with regard to the configuration of the apertures and raised portions For instance, the raised portions may have a stepped front edge to permit the fastener means to be fastened in different positions. The invention can also be applied to openable and refastenable pants-type diapers and pants-type sanitary napkins and on pants which support a diaper insert. The invention is therefore limited solely by the content of the following claims.

What is claimed is:

1. A fastener for mutually fastening together the mutually opposing front and rear side-parts of an absorbent article in the form of a diaper or a pants-type sanitary napkin, so as to bring the article to a pants-like form comprising an encircling waistband having a perimeter, wherein the article comprises a central part that includes an absorbent body, and front and rear pliable side-parts that extend from both sides of the central part, the fastener comprises two mutually coacting first and second elements, of which the first element is attached to the front side-part and the second element is attached to the rear side-part on the same side of the central part as the associated first element, wherein the first element includes a fastener portion which projects out in a direction of the perimeter of the waistband and which is insertable into an insertion opening in the associated second element in an insertion direction; said insertion opening being defined by a bottom plate having edges converging in the insertion direction of the fastener portion and two outstanding walls which extend along said converging edges perpendicular to the bottom plate; and the first element includes a substantially rectangular plate with two locking hooks side-wise projecting out from its insertion end, and the substantially rectangular plate has at least one fold which is extended in the insertion direction and has walls projecting out from the plane of the rectangular plate; and the outstanding walls of the second element comprise locking apertures coacting with the locking hooks of the first element.

2. The fastener of claim 1, wherein the substantially rectangular plate and the at least one fold are formed from one folded sheet of material.

3. The fastener of claim 2, wherein the two locking hooks are formed from the one folded sheet of material.

4. The fastener of claim 3, wherein the substantially rectangular plate and the two locking hooks are coplanar.

5. The fastener of claim 1, further comprising a second fold parallel to the at least one fold.

6. The fastener of claim 1, wherein a width of the substantially rectangular plate corresponds to a narrowest portion of the insertion opening.

7. The fastener of claim 1, wherein the substantially rectangular plate and the two locking hooks are coplanar.

8. The fastener of claim 7, wherein the substantially rectangular plate and the two locking hooks have a same thickness.

* * * * *